United States Patent [19]

Gass et al.

[11] Patent Number: 4,726,836
[45] Date of Patent: Feb. 23, 1988

[54] N-PHENYLSULFONYL-N'-PYRIMIDINYLUREAS

[75] Inventors: Karl Gass, Magden; Werner Föry, Basel; Willy Meyer, Riehen; Werner Töpfl, Dornach, all of Switzerland

[73] Assignee: Ciba-Geigy Corporation, Ardsley, N.Y.

[21] Appl. No.: 887,759

[22] Filed: Jul. 21, 1986

Related U.S. Application Data

[62] Division of Ser. No. 458,799, Jan. 18, 1983, Pat. No. 4,618,363.

[30] Foreign Application Priority Data

Jan. 25, 1982 [CH] Switzerland ............ 437/82

[51] Int. Cl.⁴ .................. A01N 43/54; C07D 239/69
[52] U.S. Cl. .......................................... 71/92; 71/90; 71/91; 544/321; 544/324; 544/323; 544/331; 544/332
[58] Field of Search ............... 71/92, 90, 91; 544/321, 544/324, 323, 331, 332

[56] References Cited

U.S. PATENT DOCUMENTS 4,500,344 2/1985 Freerksen ...................... 544/211
4,618,363 10/1986 Gass et al. ........................ 71/92

*Primary Examiner*—John M. Ford
*Attorney, Agent, or Firm*—Edward McC. Roberts; Bruce M. Collins

[57] ABSTRACT

N-Phenylsulfonyl-N'-pyrimidinylureas and -N'-triazinylureas of the general formula

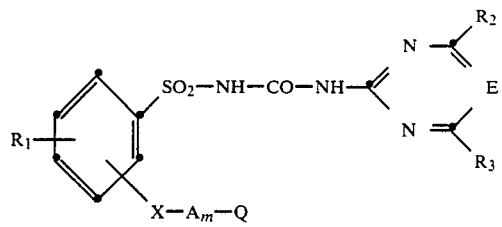

and the salts of these compounds with amines, alkali metal bases and alkaline earth metal bases or with quaternary ammonium bases, have good selective herbicidal and plant growth regulating properties when applied pre- and postemergence.

In the formula $R_1$ is hydrogen, halogen, nitro, $C_1$-$C_4$haloalkyl, $C_1$-$C_4$alkyl, $C_1$-$C_4$alkoxy, $C_2$-$C_5$alkenyl or $C_1$-$C_4$alkoxycarbonyl, $R_2$ is $C_1$-$C_2$alkyl or $C_1$-$C_3$alkoxy, each unsubstituted or substituted by 1 to 3 halogen atoms, $R_3$ is halogen, hydrogen, —$NR_4R_5$, $C_1$-$C_3$alkyl, unsubstituted or substituted by 1 to 3 halogen atoms or $C_1$-$C_4$alkoxy, or is $C_1$-$C_3$alkoxy, unsubstituted or substituted by methoxy, ethoxy, or 1 to 3 halogen atoms, $R_4$ is hydrogen or methyl, $R_5$ is hydrogen, $C_1$-$C_2$alkyl or methoxy, A is $C_1$-$C_4$alkylene or $C_2$-$C_4$alkenylene, each unsubstituted or substituted by $C_1$-$C_4$alkyl, m is 0 or 1, E is nitrogen or the methine group, X is oxygen, sulfur, —SO— or —$SO_2$—, and Q is hydroxyl, cyano or radicals selected from the group consisting of 5- or 6-membered heterocyclic rings and fused homologues, amines, acetals, esters, ketones, phenyls, sulfonic acid and carboxylic acids, which radicals may be further substituted and have functional structures.

26 Claims, No Drawings

N-PHENYLSULFONYL-N'-PYRIMIDINYLUREAS

This is a divisional of application Ser. No. 458,799 filed on Jan. 18, 1983, now U.S. Pat. No. 4,618,363.

The present invention relates to novel N-phenylsulfonyl-N'-pyrimidinyl- and -N'-triazinylureas with herbicidal and plant growth regulating properties, to the preparation thereof, to compositions containing these compounds, and to the use of the novel compounds for controlling weeds, in particular selectively, in crops of useful plants, or for regulating and inhibiting plant growth. The invention further relates to novel phenylsulfonamides obtained as intermediates.

The N-phenylsulfonyl-N'-pyrimidinyl- and -N'-triazinylureas, and salts thereof, have the general formula I

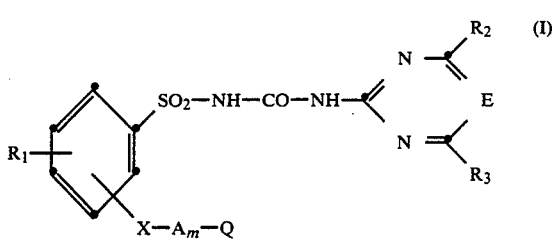

wherein
$R_1$ is hydrogen, halogen, nitro, $C_1$-$C_4$haloalkyl, $C_1$-$C_4$alkyl, $C_1$-$C_4$alkoxy, $C_2$-$C_5$alkenyl or $C_1$-$C_4$alkoxycarbonyl, $R_2$ is $C_1$-$C_3$alkyl or $C_1$-$C_3$alkoxy, each unsubstituted or substituted by 1 to 3 halogen atoms, $R_3$ is halogen, hydrogen, —$NR_4R_5$, $C_1$-$C_3$alkyl, unsubstituted or substituted by 1 to 3 halogen atoms or $C_1$-$C_4$alkoxy, or is $C_1$-$C_3$alkoxy, unsubstituted or substituted by methoxy, ethoxy, or 1 to 3 halogen atoms, $R_4$ is hydrogen or methyl, $R_5$ is hydrogen, $C_1$-$C_2$alkyl or methoxy, A is $C_1$-$C_4$alkylene or $C_2$-$C_4$alkenylene, each unsubstituted or substituted by $C_1$-$C_4$alkyl, m is 0 or 1, E is nitrogen or the methine group, X is oxygen, sulfur, —SO— or —$SO_2$, Q is hydroxyl, cyano, —$NR_6R_7$, —$SO_2$—$R_8$, —C-($OR_{10}$)$_2$—$R_{11}$, $C_2$-$C_4$alkoxyalkoxy,

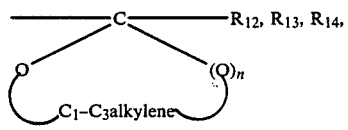

—CO—B, —CO—B', —C(B")=N—OH, —C(B")=N—(O)$_p$—$C_1$-$C_4$-alkyl, —C(B")=N—(O)$_p$—C-3-$C_5$-alkenyl, —Y—$SO_2$—$R_a$, —Y—CO—$R_b$, —Y—CO—$NR_cR_d$ or is a 5- or 6-membered heterocyclic ring or a fused homologue thereof, each linked through a carbon atom to the bridge —X—$A_m$—or, if the heterocyclic ring contains nitrogen, is also bound through a nitrogen atom, and which is unsubstituted or mono- to trisubstituted by halogen, cyano, nitro, $C_1$-$C_4$alkyl, $C_1$-$C_4$alkoxy, $C_1$-$C_4$alkylthio, $C_2$-$C_5$alkenyl, $C_1$-$C_4$haloalkyl, $C_1$-$C_4$alkoxycarbonyl, —$NR_{15}R_{16}$ or —SO—$NR_{17}R_{18}$, B is —$NR_{19}R_{20}$, —$NR_{21}$—$NR_{22}R_{23}$, —Y—$R_{24}$, $R_{25}$ or $R_{26}$, B' and B" are each $C_1$-$C_6$alkyl or $C_3$-$C_6$alkenyl, each unsubstituted or substituted by cyano, hydroxyl, —$NR_{33}R_{34}$, —$SO_2$—$NR_{35}R_{36}$, —$SO_2$—$C_1$-$C_4$-alkyl, —$SO_2$—$C_2$-$C_4$alkenyl or —$SO_2$—Ar or —CO—G, n and p are 0 or 1, $R_6$ and $R_7$, each independently of the other, are hydrogen, $C_3$-$C_6$cycloalkyl, $C_3$-$C_6$alkenyl, $C_3$-$C_6$alkynyl, or $C_1$-$C_6$alkyl, unsubstituted or substituted by $C_1$-$C_4$alkoxy, or both together are an alkylene chain which may be substituted by alkyl and/or interrupted by oxygen, sulfur, —NH— or —N($C_1$-$C_4$alkyl)-, $R_8$ is phenyl or phenyl substituted by halogen, cyano, $C_1$-$C_4$alkyl, $C_1$-$C_4$alkoxy, $C_1$-$C_4$alkylthio, $C_2$-$C_5$alkenyl, $C_1$-$C_4$haloalkyl, $C_1$-$C_4$alkoxycarbonyl, —$NR_{27}R_{28}$, —$SO_2$—$NR_{29}R_{30}$, or is —$NR_{31}R_{32}$, or with the proviso that m is 0, is also hydrogen, $C_3$-$C_6$alkynyl, or $C_1$-$C_6$alkyl or $C_3$-$C_6$alkenyl, each unsubstituted or substituted by cyano, hydroxyl, $C_1$-$C_8$alkoxy, $C_1$-$C_6$alkylthio, —$NR_{33}R_{34}$, —$SO_2$—$NR_{35}R_{36}$, —$SO_2$—$C_1$-$C_4$alkyl, —$SO_2$—$C_2$-$C_4$alkenyl, —$SO_2$—Ar or —CO—G, $R_{10}$ is hydrogen, $C_3$-$C_6$alkynyl, phenyl or phenyl substituted by halogen, nitro, cyano, $C_1$-$C_4$alkyl, $C_1$-$C_4$alkoxy, $C_1$-$C_4$alkylthio, $C_2$-$C_5$alkenyl, $C_1$-$C_4$haloalkyl, $C_1$-$C_4$alkoxycarbonyl, —$NR_{37}R_{38}$, —$SO_3H$ or —$SO_2$—$NR_{39}R_{40}$, or is $C_1$-$C_6$alkyl, $C_3$-$C_6$cycloalkyl or $C_3$-$C_6$alkenyl, each unsubstituted or substituted by cyano, hydroxyl, $C_1$-$C_6$alkoxy, $C_1$-$C_6$alkylthio, —$NR_{41}R_{42}$, —$SO_2$—$NR_{43}R_{44}$, —$SO_2$—$C_1$-$C_4$alkyl, —$SO_2$—$C_1$-$C_4$alkenyl, —$SO_2$—Ar or —CO—G, $R_{13}$ is phenyl or phenyl substituted by halogen, nitro, cyano, $C_1$-$C_4$alkyl, $C_1$-$C_4$alkoxy, $C_1$-$C_4$alkylthio, $C_2$-$C_5$alkenyl, $C_1$-$C_4$haloalkyl, $C_1$-$C_4$alkoxycarbonyl, —$NR_{45}R_{46}$, —$SO_3H$ or —$SO_2NR_{47}R_{48}$, $R_{14}$ is $C_3$-$C_6$cycloalkyl, unsubstituted or substituted by halogen or $C_1$-$C_4$alkoxy, $R_a$ and $R_b$ are each $C_3$-$C_6$cycloalkyl, $C_3$-$C_6$alkenyl, $C_3$-$C_6$alkynyl or are $C_1$-$C_6$alkyl, unsubstituted or substituted by $C_1$-$C_4$alkoxy, Y is oxygen or sulfur and G is $C_1$-$C_4$alkoxy, $C_1$-$C_4$alkylthio, $C_3$-$C_5$alkenyloxy, $C_3$-$C_5$alkenylthio, $C_1$-$C_3$alkyl, $C_3$-$C_6$alkenyl, —$NR_{49}R_{50}$, phenyl or phenyl which is mono- or disubstituted by cyano, nitro, halogen, $C_1$-$C_3$haloalkyl, $C_1$-$C_4$alkoxy, $C_1$-$C_4$alkylthio or $C_1$-$C_4$alkyl, and $R_{11}$, $R_{12}$ and $R_{24}$ have the same meanig as $R_{10}$, $R_{25}$ and Ar have the same meaning as $R_{13}$, $R_{26}$ has the same meaning as $R_{14}$, $R_c$, $R_{15}$, $R_{17}$, $R_{19}$, $R_{21}$, $R_{22}$, $R_{27}$, $R_{29}$, $R_{31}$, $R_{33}$, $R_{35}$, $R_{37}$, $R_{39}$, $R_{41}$, $R_{43}$, $R_{45}$, $R_{47}$ and $R_{49}$ have the same meaning as $R_6$;

$R_d$, $R_{16}$, $R_{18}$, $R_{20}$, $R_{23}$, $R_{28}$, $R_{30}$, $R_{32}$, $R_{34}$, $R_{36}$, $R_{38}$, $R_{40}$, $R_{42}$, $R_{44}$, $R_{46}$, $R_{48}$ and $R_{50}$ have the same meaning as $R_7$, with the proviso that Q is only hydroxyl if m is 1 and the bridge A contains at least 2 carbon atoms, and Q is only —$NR_6R_7$, —Y—$SO_2$—$R_a$, —Y—CO—$R_b$, —Y—CO—$NR_cR_d$, $C_2$-$C_4$alkoxyalkoxy or $R_{13}$ if m is 1, and that one of the radicals $R_2$ or $R_3$ is a halogen-substituted methoxy group if $R_8$ is $C_1$-$C_4$alkyl or $C_1$-$C_4$alkyl which is substituted by halogen or methoxy or is phenyl or phenyl which is substituted by methyl, methoxy, trifluoromethyl or nitro.

Herbicidally active ureas, triazines and pyrimidines are generally known in the art. Arylsulfamoyl-heterocyclylaminocarbamoyl compounds with herbicidal and plant growth-regulating action have recently been described, for example in European patent publication Nos. 1514 and 1515, U.S. Pat. No. 4 127 405, German Offenlegungsschrift No. 2 715 786 or French patent specification No. 1 468 747.

In the above definitions, alkyl denotes straight-chain or branched alkyl, e.g. methyl, ethyl, n-propyl, isopropyl, the four isomers of butyl, n-amyl, isoamyl, 2-amyl, 3-amyl, n-hexyl or isohexyl.

Alkoxy denotes methoxy, ethoxy, n-propoxy, isopropoxy and the four butoxy isomers, and is, in particular, methoxy, ethoxy or isopropoxy.

Alkylthio is e.g. methylthio, ethylthio, n-propylthio, isopropylthio and n-butylthio, with methylthio and ethylthio being preferred.

Examples of alkenyl radicals are vinyl, allyl, isopropenyl, propen-1-yl, buten-1-yl, buten-2-yl, buten-3-yl, isobuten-1-yl, isobuten-2-yl, penten-1-yl, penten-2-yl, penten-3-yl and penten-4-yl, with vinyl, allyl and penten-4-yl being preferred.

Alkylsulfonyl is e.g. methylsulfonyl, ethylsulfonyl, n-propylsulfonyl and n-butylsulfonyl, with methylsulfonyl and ethylsulfonyl being preferred.

Halogen in the above definitions by itself and in haloalkyl is fluorine, chlorine and bromine, with fluorine and chlorine being preferred.

Substituted alkyl or alkenyl radicals are those radicals which carry one or more of the cited substituents, preferably one such substituent. Where these radicals are substituted by halogen atoms, preferably several hydrogen atoms, and optionally even all hydrogen atoms, of the alkyl or alkenyl radicals are replaced by halogen.

Within the definition of alkoxycarbonyl fall such radicals as —COOCH$_3$, —COOC$_2$H$_5$, —COO—CH(CH$_3$)$_2$, —COOCH$_2$—CH$_2$—CH$_3$, —COO—(CH$_2$)$_3$—CH$_3$, —COO—CH$_2$—CH(CH$_3$)$_2$, —COO—CH(CH$_3$)—C$_2$H$_5$ and —COO—C(CH$_3$)$_3$.

Within the scope of this invention, 5- to 6-membered heterocyclic rings will be understood as meaning the following unsaturated heterocycles as well as the partially or completely hydrogenated and fused homologues thereof, e.g. furan, pyrane, thiophene, triazole, pyridine, pyrroline, oxazole, isooxazole, thiazole, isothiazole, thiadiazole, oxathiole, pyrrole, imidazole, pyrazole, pyrazine, pyrimidine, pyridazine, symmetrical and asymmetrical triazines, oxdiazole, oxazine, furazane, pyridine-N-oxide, thiophene-S-oxide, benzthiophene, benzofuran, isobenzofuran, chromene, chromane, indole, isoindole, indazole, quinoline, isoquinoline, phthalazine, quinoxaline, quinazoline, quinoline, benzthiazole and benzimidazole.

The invention also comprises the salts which the compounds of formula I are able to form with amines, alkali metal and alkaline earth metal bases or with quaternary ammonium bases.

Preferred salt-forming alkali metal and alkaline earth metal hydroxides are the hydroxides of lithium, sodium, potassium, magnesium or calcium, most preferably of sodium or potassium.

Examples of suitable salt-forming amines are primary, secondary and tertiary aliphatic and aromatic amines such as methylamine, ethylamine, propylamine, isopropylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which either
(a) X is oxygen,
(b) R$_1$ is hydrogen or
(c) the substituent —X—A$_m$—Q is in the 2-position to the sulfonyl group
or
(d) R$_2$ and R$_3$ together contain at most 4 carbon atoms.

Further preferred compounds of the formula I are those in which X is oxygen and R$_1$ is hydrogen, the substituent —X—A$_m$—Q is in the 2-position to the sulfonyl group and R$_2$ and R$_3$ together contain not more than 4 carbon atoms.

Among these last mentioned compounds, those compounds are particularly preferred in which A is a C$_1$-C$_2$alkylene bridge, m is 1, E is the methine group and Q is cyano or C$_1$-C$_4$alkoxycarbonyl.

As a preferred subgroup of the formula I, those compounds also merit attention in which R$_1$ is hydrogen or chlorine or methyl bound in the 5-position, R$_2$ is methyl or methoxy, R$_3$ is methyl, methoxy, chlorine, difluoromethoxy, dimethylamino or ethoxy, X is oxygen, A is a direct bond or a straight chain or branched C$_1$-C$_5$alkylene bridge or a propylene bridge, and Q is cyano, ethoxycarbonyl, methoxycarbonyl, acetyl, benzoyl, methylsulfonyl, hydroxyl, dimethylcarbamoyl, propylsulfonyl, 3,5-dichloropyrid-2-yl, 2,2-dichlorocyclopropyl, isobutyroyl, pyrid-2-yl, pyrid-3-yl, pyrid-4-yl, methylsulfonyloxy, acetoxy, oxiranyl, tetrahydrofuran-2-yl, tetrahydrofuran-3-yl, 2-methyl-1,3-dioxolan-2-yl, 2,2-dimethyl-1,3-dioxolan-4-yl, 1-hydroxyiminoethyl, 1-ethoxyiminoethyl, 1-allyloxyiminoethyl, methoxyethoxy, 1-propyliminoethyl, 1,3-dioxolan-2-yl, 5-ethyl-2-methyl-1,3-dioxolan-2-yl, 2-methyl-2-oxiranyl, 3-methyl-2-oxiranyl, 2-isopropyl-1,3-dioxolan-2-yl, 1-ethoxyimino-isobutyl, dimethylamino or N-methylcarbamoyloxy.

Most preferred, however, is the subgroup of compounds of the formula I, wherein R$_1$ is hydrogen or methyl bound in the 5-position, R$_2$ is methyl or methoxy, R$_3$ is methyl, methoxy, chlorine, difluoromethoxy or dimethylamino, X is oxygen, A is a direct bond or a straight chain or branched C$_1$-C$_3$alkylene bridge and Q is cyano, ethoxycarbonyl, methoxycarbonyl, acetyl, benzoyl, methylsulfonyl, hydroxyl, dimethylcarbamoyl, propylsulfonyl, 3,5-dichloropyrid-2-yl, 2,2-dichlorocyclopropyl, isobutyroyl, pyrid-2-yl, pyrid-3-yl, pyrid-4-yl, methylsulfonyloxy, acetoxy, oxiranyl, 2-methyl-1,3-dioxolan-2-yl, 1-hydroxyiminoethyl, 1-ethoxyiminoethyl, 1-allyloximinoethyl, methoxyethoxy or N-methylcarbamoyloxy.

Preferred individual compounds are:
N-(2-oxiranylmethoxyphenylsulfonyl)-N'-(4-methoxy-6-methyl-1,3,5-triazin-2-yl)urea,
N-(2-oxiranylmethoxyphenylsulfonyl)-N'-(4-methoxy-6-methylpyrimidin-2-yl)urea,
N-(2-oxiranylmethoxyphenylsulfonyl)-N'-(4'-ethoxy-6-methyl-1,3,5-triazin-2-yl)urea,
N-(2-oxiranylmethoxyphenylsulfonyl)-N'-(4-difluoromethoxy-6-methylpyrimidin-2-yl)urea,
N-(2-methoxyethoxymethoxyphenylsulfonyl)-N'-(4-methoxy-6-methyl-1,3,5-triazin-2-yl)urea,
and
N-(2-methoxyethoxymethoxyphenylsulfonyl)-N'-(4-difluoromethoxy-6-methylpyrimidin-2-yl)urea.

The process for obtaining the compounds of formula I is carried out in an inert organic solvent.

In a first process, the compounds of the formula I are obtained by reacting a phenylsulfonamide of the formula II

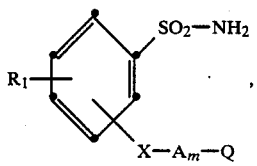

wherein A, $R_1$, Q, X and m are as defined for formula I, in the presence of a base, with an N-pyrimidinyl- or N-triazinylcarbamate of the formula III

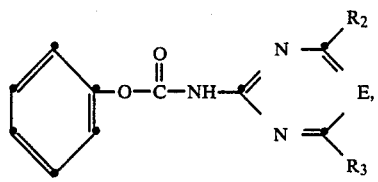

wherein E, $R_2$ and $R_3$ are as defined for formula I.

In a second process, compounds of formula I are obtained by reacting a phenylsulfonylisocyanate or phenylsulfonylisothiocyanate of the formula IV

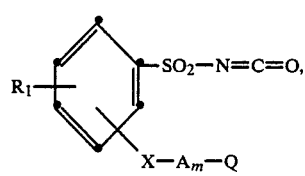

wherein A, $R_1$, Q, m and X are as defined for formula I, optionally in the presence of a base, with an amine of the formula V

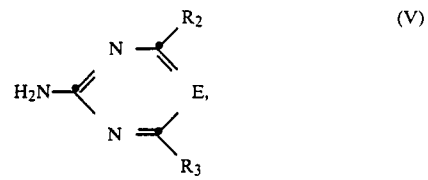

wherein E, $R_2$ and $R_3$ are as defined for formula I.

In a further process, the compounds of formula I are obtained by reacting a sulfonamide of the formula II above, optionally in the presence of a base, with an isocyanate or isothiocyanate of the formula VI

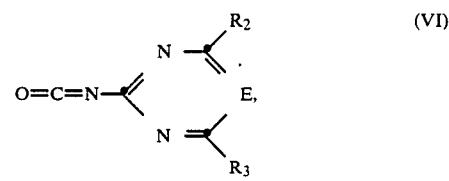

wherein E, $R_2$ and $R_3$ are as defined for formula I.

Finally, the compounds of formula I can also be obtained by reacting a N-phenylsulfonylcarbamate of the formula VII

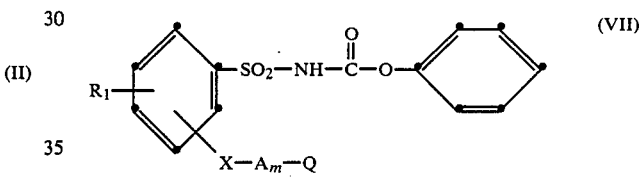

wherein A, $R_1$, Q, m and X as defined for formula I, with an amine of the formula V above.

If desired, the ureas of formula I can be converted into basic addition salts with amines, alkali metal hydroxides or alkaline earth metal hydroxides or with quaternary ammonium bases. This conversion is carried out e.g. by reacting the compounds of formula I with the equimolar amount of a base and removing the solvent by evaporation.

Some of the starting materials of the formulae II, IV and VII are novel and can be prepared by the following methods.

The novel sulfonamides of formula II used as intermediates are obtained from the corresponding anilines by diazotisation and replacement of the diazo group, with sulfur dioxide, in the presence of a catalyst such as copper(I) chloride, in hydrochloric acid or acetic acid, and reacting the resultant phenylsulfonyl chloride with ammonium hydroxide solution.

The compounds of formula II can also be obtained by O- or S-alkylation or O- or S-alkenylation of hydroxy- or thiophenylsulfonamides with the corresponding halides or sulfuric acid esters or which corresponding activated alkenyl or alkynyl compounds by 1,2-addition, or by reaction of ortho-halophenylsulfonamides with metal alcoholates or mercaptides and, if desired, by oxidation thereof e.g. with periodates or peracids, to give the corresponding sulfoxides and sulfones.

Ortho-substituted hydroxyphenylsulfonamides or substituted ortho-hydroxyphenylsulfonamides of the formula VIII

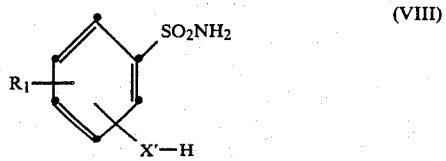

(VIII)

wherein $R_1$ is as defined for formula I and $X'$ is oxygen or sulfur, are described as starting materials for specific sulfonamide representatives of the formula II in European patent application No. 44807.

Some of the compounds of formula II used as intermediates are novel and have been specially developed for the synthesis of compounds of the formula I. The novel intermediates of the narrower subformula IIa

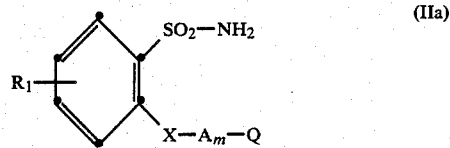

(IIa)

wherein $R_1$, A, m, X and Q are as defined for formula I, with the proviso that $R_1$ is not hydrogen if the radical $-X-A_m-Q$ is benzyloxy, constitute a further object of the present invention.

The phenylsulfonylisocyanates of the formula IV, which are also novel, may be obtained by reacting the sulfonamides of the formula II with phosgene, in the presence of butyl isocyanate in a chlorinated hydrocarbon, at reflux temperature. Similar reactions are described in "Recent Methods of Preparative Organic Chemistry", Vol. VI, 211–229, Academic Press, New York and London.

The novel isothiocyanates of the formula IV are obtained by treating the sulfonamides of formula II with carbon disulfide and potassium hydroxide and subsequently reacting the dipotassium salt with phosgene. Such processes are described in Arch. Pharm. 299, 174 (1966).

The novel N-phenylsulfonyl carbamates of the formula VII are obtained by reacting the sulfonamides of the formula II with diphenyl carbamate in the presence of a base. Similar processes are described in Japanese patent specification No. 61 169.

The starting materials of the formulae III, V and VI are known or they may be prepared by known methods.

Isocyanates of the formula VI may be prepared by reacting amines of the formula V with oxalyl chloride in a chlorinated hydrocarbon as solvent. Amines of the formula V are known and some are commercially available, or they can be prepared by known methods, q.v. "The Chemistry of Heterocyclic Compounds", Vol. XIV, Interscience Publishers, New York, London.

It is expedient to carry out the reactions for obtaining compounds of formula I in aprotic, inert organic solvents such as methylene chloride, tetrahydrofuran, acetonitrile, dioxan or toluene.

The reaction temperatures are preferably in the range from $-20°$ to $+120°$ C. The reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The final products can be isolated by concentrating the reaction mixture and/or removing the solvent by evaporation, and by recrystallising or triturating the solid residue in a solvent in which it is poorly soluble, such as an ether, an aromatic hydrocarbon or a chlorinated hydrocarbon.

The compounds of formula I are stable compounds, and no protective measures are required for handling them.

When used in low rates of application, the compounds of formula I have good selective growth-inhibiting and selective herbicidal properties which make them most suitable for use in crops of useful plants, especially in cereals, cotton, soybeans, maize and rice. In some cases damage is also caused to weeds which have up to now have only been controlled with total herbicides.

In addition, the compounds of formula I have pronounced plant growth regulating properties which can lead to an increase in the yield of cultivated plants and harvested crops. Further, many compounds of formula I have a plant growth inhibiting action which is dependent on concentration. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops are unable to compete with the cultivated plants.

In many cultivated plants inhibition of vegetative growth permits more plants to be sown in a crop area, so that a higher yield may be obtained per unit of area. A further mechanism of yield increase using growth regulators resides in the fact that nutrients are able increasingly to promote flower formation and fruiting, whilst vegetable growth is restricted.

Inhibition of the vegetative growth of monocot plants, e.g. grasses or cereals, is sometimes desirable and advantageous. Such a growth inhibition is of economic interest, inter alia, in respect of grasses, as the frequency of cutting in flower gardens, parks, sports fields or road shoulders can thereby be reduced. Of importance too is the inhibition of growth of herbaceous and ligneous plants on road shoulders and near transmission lines, or generally in areas in which strong growth is undersirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals and this too counteracts lodging.

Further, the compounds of formula I are suitable for preventing stored potatoes from seeding. During winter storage, potatoes often develop sprouts which result in shrinkage, weight loss, and rot.

When the compounds of formula I are applied in higher rates of application, all tested plants are so damaged in their development that they wither.

The mode of action of these compounds is unusual. Many are translocatable, i.e. they are absorbed by the plant and transported to other parts of it where they then deploy their action. The unusual feature of the compounds is that they do not only take the path through the vascular bundle in the ligneous part from the roots to the leaves, but can also be translocated through the sieve tubes in the bast part of the leaves back into the roots. Thus, for example, it is possible to damage perennial weeds to the roots by surface treatment. Compared with other herbicides and growth regulators, the novel compounds of the formula I are effective even when used in very low rates of application.

The invention also relates to herbicidal and plant growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosed in accordance with the intended objectives and the prevailing circumstances.

The formulations i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepolite or bentonite; and suitable non-sorbent carriers are materials such as calcite or sand. In addition, a great number of preganulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl laurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$-alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ridgewood, N.J. 1979; Sisley and Wood, "Encyclopedia of Surface Active Agents", Chemical Publishing Co. Inc., New York, 1964.

The pesticidal formulations usually contain 0.1 to 95%, preferably 0.1 to 80%, of a compound of the formula I, 1 to 99.9% of a solid or liquid adjuvant, and 0 to 25%, preferably 0.1 to 25%, of a surfactant.

Preferred formulations are composed in particular of the following constituents (%=percentage by weight):
Solutions
  active ingredient: 1 to 30%, preferably 5 to 20%
  solvent: 99 to 0%, preferably 95 to 0%
  surfactants: 1 to 99%, preferably 0 to 95%
Emulsifiable concentrates
  active ingredient: 1 to 20%, preferably 5 to 10%
  surfactant: 5 to 30%, preferably 10 to 20%
  liquid carrier: 50 to 94%, preferably 70 to 85%
Dusts
  active ingredient: 0.1 to 10%, preferably 0.1 to 1%
  solid carrier: 99.9 to 90%, preferably 99.9 to 99%
Suspension concentrates
  active ingredient: 5 to 75%, preferably 10 to 50%
  water: 94 to 25%, preferably 90 to 30%
  surfactant: 1 to 40%, preferably 2 to 30%
Wettable powders
  active ingredient: 0.5 to 90%, preferably 1 to 80%
  surfactant: 0.5 to 20%, preferably 1 to 15%
  solid carrier: 5 to 95%, preferably 15 to 90%
Granulates
  active ingredient: 0.5 to 30%, preferably 3 to 15%
  solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.01 to 10 kg a.i./ha, preferably 0.025 to 5 kg a.i./ha.

The compositions can also contain further ingredients such as stabilisers, antifoams, viscosity regulators, binders, adhesives, as well as fertilisers or other active compounds, in order to attain special effects.

PREPARATORY EXAMPLES

EXAMPLE 1

(a) 2-(1-Methoxycarbonylethoxy)benzenesulfonamide 34.6 g of 2-hydroxybenzenesulfonamide and 55.3 g of potassium carbonate are added to 800 ml of acetonitrile. With efficient stirring, 33.4 g of methyl 2-bromopropionate are added dropwise over 10 minutes and the suspension is then heated for 5 hours to 45° C. After the reaction mixture has cooled, the precipitated salts are isolated and the filtrate is concentrated in vacuo. The residue is recrystallised from ethanol, affording 41.8 g of 2-(1-methoxycarbonylethoxy)-benzenesulfonamide with a melting point of 140°–142° C.

(b) 2-(1-Methoxycarbonylethoxy)benzenesulfonyl isocyanate

A mixture of 12.9 g of 2-(1-methoxycarbonylethoxy)-benzenesulfonamide, 4.9 g of n-butylisocyanate and 0.1 g of diazabicyclooctane and 130 ml of xylene is refluxed for 30 minutes. Then 10 g of phosgene are passed into the solution at the same temperature over 90 minutes. Excess phosgene is expelled with nitrogen and the solution is then cooled and concentrated in vacuo, affording 17.7 g of 2-(1-methoxycarbonylethoxy)benzenesulfonyl isocyanate in the form of a brownish oil which can be further used without purification.

(c) N-[2-(1-Methoxycarbonylethoxy)phenylsulfonyl]-N'-(4,6-dimethylpyrimidin-2-yl)urea (compound 104)

With stirring, a soluton of 8.8 g of 2-(methoxycarbonylethoxy)benzenesulfonyl isocyanate in 40 ml of absolute tetrahydrofuran is adeed dropwise to a solution of 3.1 g of 2-amino-4,6-dimethylpyridine and 0.1 g of diazabicyclooctane in 50 ml of tetrahydrofuran. In the course of this addition the temperature of the solution rises from 20° to 25° C. After stirring for 3 hours at room temperature, the solvent is stripped off and the residue is crystallised from ethyl acetate, affording 5.2 g of N-[2-(1-methoxycarbonylethoxy)phenylsulfonyl]-N'-(4,6-dimethylpyrimidin-2-yl)urea with a melting point of 200°–203° C.

EXAMPLE 2

2-Oxiranylmethoxyphenylsulfonamide

To a mixture of 15.3 g of 3-chloroperbenzoic acid in 270 ml of absolute methylene chloride are added 14.2 g of 2-allyloxyphenylsulfonamide over 2 minutes. The solution is then heated to reflux for 3 hours, cooled, and then washed three times with saturated sodium carbonate solution and once with water. The organic phase is dried and concentrated, affording 11.9 g of 2-oxiranylmethoxyphenylsulfonamide with a melting point of 132°–133° C.

EXAMPLE 3

(a) 2-(2-Methyl-1,3-dioxolan-2-yl-methoxy)phenylsulfonamide

A mixture of 4.58 g of 2-(2-propanon-1-yloxy)phenylsulfonamide, 2 ml of ethylene glycol, 0.02 g of p-toluenesulfonic acid and 30 ml of toluene is heated for 7 hours to reflux while simultaneously separating the water of reaction. The cooled solution is taken up in 80 ml of ethyl acetate and the organic phase is washed with saturated sodium bicarbonate solution and water, dried and concentrated, affording 5 g of 2-(2-methyl-1,3-dioxolan-2-yl-methoxy)phenylsulfonamide in the form of a yellow viscous oil which can be further used without purification.

(b) N-[2-(2-Methyl-1,3-dioxolan-2-yl-methoxy)-phenylsulfonyl]-N'-(4-methoxy-6-methyl-1,3,5-triazin-2-yl)urea 2.73 g of N-(2-methoxy-6-methyl-1,3,5-triazin-2-yl)-O-phenylcarbamate are added to 2.73 g of crude 2-(2-methyl-1,3-dioxolan-2-yl-methoxy)-phenylsulfonamide and 1.56 ml of 1,8-diazabicyclo(5.4.0)undec-7-ene in absolute dioxan. The mixture is stirred for 1 hour at 20°–25° C. and then a mixture of 15 ml of water and 5 ml of 2N hydrochloric acid is added. The precipitate is isolated and washed with ether, affording 4 g of the title compound with a melting point of 135°–136° C.

The intermediate of the formula I and final products of the formula I listed in the following tables are obtained in corresponding manner:

TABLE 1

(structure: phenyl ring with $SO_2-NH_2$ and $X-A_m-Q$ substituents)

| No. | A | Q | X | m | m.p. (°C.) |
|---|---|---|---|---|---|
| 1 | —CH₂— | —CN | O | 1 | 192–195° |
| 2 | —CH₂— | —COOC₂H₅ | O | 1 | 119–121° |
| 3 | —CH₂— | —CH₃ | O | 1 | 174–176° |
| 4 | —CH(CH₃)— | —COOCH₃ | O | 1 | 140–142° |
| 5 | —CH(CH₃)— | —COOC₂H₅ | O | 1 | |
| 6 | —CH₂— | —C₆H₅ | O | 1 | |
| 7 | —CH₂— | 4-CH₃—C₆H₄— | O | 1 | |
| 8 | —CH₂— | (1,3-dioxolan-2-yl) | O | 1 | |
| 9 | —CH₂— | —CO—CH₃ | O | 1 | 153–154° |
| 10 | —CH₂— | —CO—C₆H₅ | O | 1 | 180–181° |
| 11 | —CH₂—CH₂— | —CN | O | 1 | |
| 12 | —CH₂—CH₂— | —COOCH₃ | O | 1 | |
| 13 | —CH₂—CH₂— | —CO—C₆H₅ | O | 1 | |
| 14 | — | —SO₂—CH₃ | O | 0 | 134–136° |
| 15 | —CH₂— | (cyclopropyl-Cl,Cl) | O | 1 | 111° |
| 16 | —CH₂—CH₂— | —OH | O | 1 | 100–101° |
| 17 | —CH₂— | —CH(OC₂H₅)₂ | O | 1 | |
| 18 | —CH=CH— | —CO—CH₃ | O | 1 | |
| 19 | —CH₂— | —PO(OC₂H₅)₂ | O | 1 | |
| 20 | —CH₂— | —PO(OH)₂ | O | 1 | |
| 21 | —CH₂— | —N(tribromotriazinyl) | O | 1 | |
| 22 | —CH₂— | —N(trichlorotriazinyl) | O | 1 | |

TABLE 1-continued

Structure: benzene ring with SO$_2$—NH$_2$ and X—A$_m$—Q substituents

| No. | A | Q | X | m | m.p. (°C.) |
|---|---|---|---|---|---|
| 23 | —CH$_2$— | 3-bromo-5,6-dichloropyridazin-1-yl | O | 1 | |
| 24 | —CH$_2$— | 3-isopropyl-5-chloropyridazin-1-yl | O | 1 | |
| 25 | —CH$_2$— | 5-methylthio-1,3,4-thiadiazol-2-yl (N-linked) | O | 1 | |
| 26 | —CH$_2$— | succinimido | O | 1 | |
| 27 | —CH$_2$— | phthalimido | O | 1 | |
| 28 | — | 5-tert-butyl-1,3,4-thiadiazol-2-yl | O | 1 | |
| 29 | — | 5-trifluoromethyl-1,3,4-thiadiazol-2-yl | O | 0 | |
| 30 | — | 6-chloropyridazin-3-yl | O | 0 | |
| 31 | — | 5-trifluoromethyl-1,3,4-thiadiazol-2-yl | O | 0 | |
| 32 | — | 5-methoxy-1,3,4-thiadiazol-2-yl | O | 0 | |

TABLE 1-continued

[structure: benzene ring with SO₂—NH₂ and X—A$_m$—Q substituents]

| No. | A | Q | X | m | m.p. (°C.) |
|-----|---|---|---|---|------------|
| 33 | — | 2,6-dichloropyrimidin-4-yl | O | 0 | |
| 34 | — | 2-pyridyl | O | 0 | 161–162° |
| 35 | — | 3,6-dichloropyridazin-yl | O | 0 | 158–167° |
| 36 | — | 3-trifluoromethylpyridazin-yl | O | 0 | 196–200° |
| 37 | — | 5-chloro-3-trifluoromethylpyridazin-yl | O | 0 | |
| 38 | — | thiazol-2-yl | O | 0 | |
| 39 | — | 3-cyanopyridazin-yl | O | 0 | |
| 40 | — | 2-methoxy-6-chloropyrimidin-4-yl | O | 0 | |
| 41 | — | 2-methoxy-6-dimethylaminopyrimidin-4-yl | O | 0 | |

TABLE 1-continued

[Structure: benzene ring with SO$_2$-NH$_2$ substituent and X-A$_m$-Q substituent]

| No. | A | Q | X | m | m.p. (°C.) |
|---|---|---|---|---|---|
| 42 | — | [4,6-dichloro-1,3,5-triazin-2-yl] | O | 0 | |
| 43 | — | [4-methyl-6-amino-1,3,5-triazin-2-yl] | O | 0 | |
| 44 | — | [2-amino-6-methoxy-pyrimidin-4-yl] | O | 0 | |
| 45 | — | [4-chloro-6-amino-1,3,5-triazin-2-yl] | O | 0 | |
| 46 | — | [2-amino-6-chloro-pyrimidin-4-yl] | O | 0 | |
| 47 | —CH$_2$— | —CO—N(CH$_3$)$_2$ | O | 1 | 165–166° |
| 48 | —CH$_2$— | —O—CO—((CH$_3$)$_3$) | O | 0 | 106–107° |
| 49 | —CH$_2$—CH$_2$— | —O—CO—CH$_3$ | O | 1 | 93–94° |
| 50 | —CH$_2$—CH$_2$— | —O—CO—NH—CH$_3$ | O | 1 | 170–172° |
| 51 | —CH$_2$—CH$_2$— | —N(CH$_3$)$_2$ | O | 1 | 143–145° |
| 52 | — | —CO—N(CH$_3$)$_2$ | O | 0 | 148–150° |
| 53 | —CH$_2$—CH$_2$— | —O—CO—CH$_3$ | SO$_2$ | 1 | 140–141° |
| 54 | —CH$_2$—CH$_2$— | —O—CO—CH$_3$ | S | 1 | 133–135° |
| 55 | —CH$_2$—CH$_2$— | —O—SO$_2$—CH$_3$ | O | 1 | 126–127° |
| 56 | —CH$_2$— | [oxiranyl] | O | 1 | 132–133° |
| 57 | —CH$_2$— | 3-pyridyl | O | 1 | 131–132° |
| 58 | —CH$_2$— | 2-pyridyl | O | 1 | 138–139° |
| 59 | —CH$_2$— | 4-pyridyl | O | 1 | 204–206° |
| 60 | —CH$_2$— | [N-methylpiperidinyl] | O | 1 | 171–173° |
| 61 | —CH$_2$— | —CO—C$_3$H$_7$—i | O | 1 | 109–113° |
| 62 | —CH$_2$— | 2-thienyl | O | 1 | 127–129° |

TABLE 1-continued

[Structure: benzene ring with SO₂—NH₂ and X—A$_m$—Q substituents]

| No. | A | Q | X | m | m.p. (°C.) |
|---|---|---|---|---|---|
| 63 | —CH₂—CH₂— | OH | S | 1 | oil |
| 64 | —CH₂—CH₂— | —O—(CH₂)₂—OCH₃ | O | 1 | 68–69° |
| 65 | — | tetrahydrofuran-3-yl | O | 0 | |
| 66 | — | tetrahydrofuran-3-yl | S | 0 | |
| 67 | — | tetrahydrofuran-3-yl | SO₂ | 0 | |
| 68 | —CH₂— | 2-tetrahydrofuranyl | O | 1 | |
| 69 | —CH₂— | —C(CH₃H₇—i)=N—OC₂H₅ | O | 1 | |
| 70 | —CH₂— | [1,3-dioxolan-2-yl with C₃H₇—i] | O | 1 | |
| 71 | —(CH₂)₃— | —COOC₂H₅ | O | 1 | 100–101° |
| 72 | —CH(C₂H₅)— | —COOC₂H₅ | O | 1 | 105–106° |
| 73 | (X)—CH₂—CH=CH—(Q) | —COOCH₃ | O | 1 | 162–165° |
| 74 | —CH₂— | [1,3-dioxolan-2-yl with CH₃] | O | 1 | oil |
| 75 | —CH₂— | —C(CH₃)=N—OH | O | 1 | 191–192° |
| 76 | —CH₂— | —C(CH₃)=N—OC₂H₅ | O | 1 | 120–121° |
| 77 | —CH₂— | —C(CH₃)=N—O—CH₂—CH=CH₂ | O | 1 | 124°126° |
| 78 | —CH₂— | —O(CH₂)₂—OCH₃ | O | 1 | 80–84° |
| 79 | —CH₂— | —C(CH₃)=N—C₃H₇—n | O | 1 | |
| 80 | —CH₂— | [1,3-dioxolane with two CH₃ groups] | O | 1 | 78–80° |
| 81 | —CH₂— | [dioxolane with H] | O | 1 | oil |
| 82 | —CH₂— | [dioxolane with CH₃ and C₂H₅] | O | 1 | oil |
| 83 | —CH₂— | [oxirane with CH₃] | O | 1 | 102–103° |
| 84 | —CH₂— | [oxirane with CH₃] | O | 1 | 111–112° |
| 85 | —CH₂— | [dioxolane with CH₃ and C₃H₇—n] | O | 1 | oil |

TABLE 1-continued

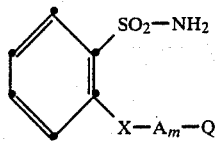

| No. | A | Q | X | m | m.p. (°C.) |
|---|---|---|---|---|---|
| 86 | —CH₂— | 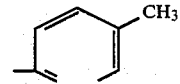 | O | 1 | 107–109° |
| 87 | —CH₂—CH₂— | 2-pyridyl | O | 0 | |
| 88 | —CH₂— | 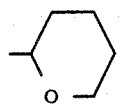 | O | 1 | |
| 89 | —CH₂— | 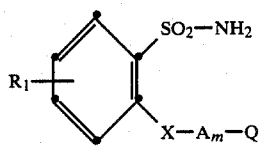 | O | 1 | 149–150° |

TABLE 2

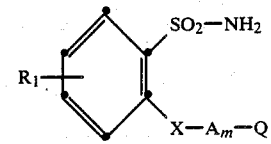

| No. | A | Q | R₁ | X | m | m.p. (°C.) |
|---|---|---|---|---|---|---|
| 90 | —CH₂— | —COOCH₃ | 5-CH₃ | O | 1 | 168–169° |
| 91 | —CH₂—CH₂— | —COOCH₃ | 5-CH₃ | O | 1 | |
| 92 | —CH₂— | —CN | 5-Cl | O | 1 | |
| 93 | —CH₂— | —COOCH₃ | 5-F | O | 1 | |

TABLE 3

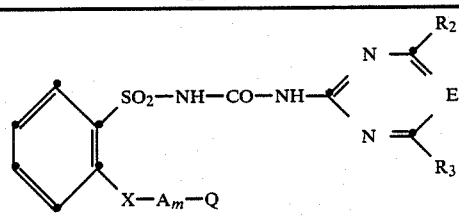

| No. | A | Q | X | m | R₂ | R₃ | E | m.p. (°C.) |
|---|---|---|---|---|---|---|---|---|
| 101 | —CH₂— | —CN | O | 1 | CH₃ | CH₃ | CH | 175–178° |
| 102 | —CH₂— | —COOC₂H₅ | O | 1 | CH₃ | CH₃ | CH | 153–154° |
| 103 | —CH₂— | —COOCH₃ | O | 1 | CH₃ | CH₃ | CH | 194–196° |
| 104 | —CH(CH₃)— | —COOCH₃ | O | 1 | CH₃ | CH₃ | CH | 200–203° |
| 105 | —CH(CH₃)— | —COOCH₃ | O | 1 | CH₃ | OCH₃ | CH | 180–182° |
| 106 | —CH(CH₃)— | —COOCH₃ | O | 1 | CH₃ | OCH₃ | N | 165–167° |
| 107 | —CH(CH₃)— | —COOCH₃ | O | 1 | OCH₃ | OCH₃ | N | 163–165° |
| 108 | —CH(CH₃)— | —COOCH₃ | O | 1 | OCH₃ | OCH₃ | CH | |
| 109 | —CH(CH₃)— | —COOCH₃ | O | 1 | OCH₃ | —N(CH₃)₂ | N | 175–176° |
| 110 | —CH(CH₃)— | —COOCH₃ | O | 1 | OCH₃ | Cl | CH | |
| 111 | —CH₂— | —CN | O | 1 | CH₃ | OCH₃ | CH | 168–170° |
| 112 | —CH₂— | —CN | O | 1 | OCH₃ | OCH₃ | CH | 180–181° |
| 113 | —CH₂— | —CN | O | 1 | CH₃ | OCH₃ | N | 188–190° |
| 114 | —CH₂— | —CN | O | 1 | OCH₃ | OCH₃ | N | 188° |
| 115 | —CH₂— | —CN | O | 1 | OCH₃ | —N(CH₃)₂ | N | >220° |
| 116 | —CH₂— | —COOC₂H₅ | O | 1 | OCH₃ | —N(CH₃)₂ | N | |

TABLE 3-continued

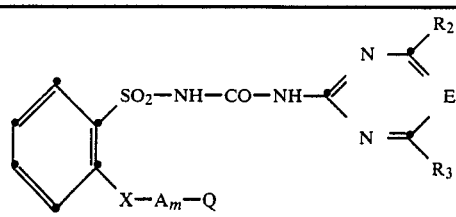

| No. | A | Q | X | m | | | E | m.p. (°C.) |
|---|---|---|---|---|---|---|---|---|
| 117 | —CH$_2$— | —COOC$_2$H$_5$ | O | 1 | OCH$_3$ | OCH$_3$ | N | 157–159° |
| 118 | —CH$_2$— | —COOC$_2$H$_5$ | O | 1 | OCH$_3$ | OCH$_3$ | CH | 160–162° |
| 119 | —CH$_2$— | —COOC$_2$H$_5$ | O | 1 | OCH$_3$ | CH$_3$ | CH | 164–165° |
| 120 | —CH$_2$— | —COOC$_2$H$_5$ | O | 1 | OCH$_3$ | CH$_3$ | N | 136–137° |
| 121 | —CH$_2$— | —COOC$_2$H$_5$ | O | 1 | OCH$_3$ | OCH$_3$ | N | |
| 122 | — | —SO$_2$CH$_3$ | O | 0 | OCH$_3$ | OCH$_3$ | N | |
| 123 | — | —SO$_2$CH$_3$ | O | 0 | OCH$_3$ | OCH$_3$ | CH | |
| 124 | —CH$_2$— | —CO—CH$_3$ | O | 1 | CH$_3$ | OCH$_3$ | CH | |
| 125 | —CH$_2$— | —CO—CH$_3$ | O | 1 | CH$_3$ | OCH$_3$ | N | 163–165° |
| 126 | —CH$_2$— | —CO—CH$_3$ | O | 1 | OCH$_3$ | OCH$_3$ | N | |
| 127 | —CH$_2$— | —CO—CH$_3$ | O | 1 | OCH$_3$ | OCH$_3$ | CN | |
| 128 | —CH$_2$— | —CO—CH$_3$ | O | 1 | OCH$_3$ | —N(CH$_3$)$_2$ | N | |
| 129 | —CH$_2$— | —CO—C$_6$H$_5$ | O | 1 | OCH$_3$ | —N(CH$_3$)$_2$ | N | |
| 130 | —CH$_2$ | —CO—C$_6$H$_5$ | O | 1 | OCH$_3$ | OCH$_3$ | N | |
| 131 | —CH$_2$— | —CO—C$_6$H$_5$ | O | 1 | OCH$_3$ | OCH$_3$ | CH | |
| 132 | —CH$_2$— | —CO—C$_6$H$_5$ | O | 1 | OCH$_3$ | CH$_3$ | CH | |
| 133 | —CH$_2$— | —CO—C$_6$H$_5$ | O | 1 | OCH$_3$ | CH$_3$ | N | 180–184° |
| 134 | —CH$_2$—CH$_2$— | —OH | O | 1 | OCH$_3$ | OCH$_3$ | CH | 137–139° |
| 135 | —CH$_2$—CH$_2$— | —OH | O | 1 | CH$_3$ | OCH$_3$ | N | 155° (decomp.) |
| 136 | —CH$_2$—CH$_2$— | —O—CO—CH$_3$ | O | 1 | CH$_3$ | OCH$_3$ | N | 157° (decomp.) |
| 137 | —CH$_2$—CH$_2$— | —O—CO—NH—CH$_3$ | O | 1 | CH$_3$ | OCH$_3$ | N | 176–177° |
| 138 | — | —CO—N(CH$_3$)$_2$ | O | 0 | CH$_3$ | OCH$_3$ | CH | 191–192° |
| 139 | —CH$_2$—CH$_2$— | —N(CH$_3$)$_2$ | O | 1 | OCH$_3$ | OCH$_3$ | CH | >250° |
| 140 | —(CH$_2$)$_3$— | —CN | O | 1 | OCH$_3$ | CH$_3$ | N | 165° |
| 141 | —CH$_2$— | —COOCH$_3$ | O | 1 | OCH$_3$ | CH$_3$ | N | 178–179° |
| 142 | —CH$_2$— | —COOCH$_3$ | O | 1 | OCH$_3$ | —N(CH$_3$)$_2$ | N | 186–187° |
| 143 | —CH$_2$— | —CO—N(CH$_3$)$_2$ | O | 1 | OCH$_3$ | OCH$_3$ | CH | 144–147° |
| 144 | —CH$_2$— | —CO—C$_6$H$_5$ | O | 1 | OCH$_3$ | Cl | CH | 168–173° |
| 145 | —CH$_2$— | —CO—C$_6$H$_5$ | O | 1 | OCH$_3$ | —N(CH$_3$)$_2$ | N | 200–205° |
| 146 | — | (3,5-dichloropyridin-2-yl) | O | 0 | OCH$_3$ | CH$_3$ | N | 187–189° |
| 147 | —CH$_2$— | (2,2-dichlorocyclopropyl) | O | 1 | OCH$_3$ | CH$_3$ | N | 140° C. |
| 148 | —CH$_2$— | —CO—N(CH$_3$)$_2$ | O | 1 | OCH$_3$ | CH$_3$ | N | 164–166° |
| 149 | — | —SO$_2$—CH$_3$ | O | 0 | OCH$_3$ | OCHF$_2$ | CH | 155–165° |
| 150 | — | —SO$_2$—C$_3$H$_7$—n | O | 0 | OCH$_3$ | OCHF$_2$ | CH | 189–191° |
| 151 | —CH$_2$—CH$_2$— | —O—SO$_2$—CH$_3$ | O | 1 | OCH$_3$ | CH$_3$ | N | 181–182° |
| 152 | —CH$_2$—CH$_2$— | —O—CO—CH$_3$ | S | 1 | OCH$_3$ | CH$_3$ | N | 137–139° |
| 153 | —CH$_2$—CH$_2$ | —O—CO—CH$_3$ | SO$_2$ | 1 | OCH$_3$ | CH$_3$ | N | 105–107° |
| 154 | —CH$_2$— | 4-pyridyl | O | 1 | OCH$_3$ | CH$_3$ | N | 204–205° |
| 155 | —CH$_2$— | 3-pyridyl | O | 1 | OCH$_3$ | CH$_3$ | CH | 189–190° |
| 156 | —CH$_2$— | 2-pyridyl | O | 1 | OCH$_3$ | CH$_3$ | CH | 190–193° |
| 157 | —CH$_2$— | 3-pyridyl | O | 1 | OCH$_3$ | CH$_3$ | N | 185–187° |
| 158 | —CH$_2$— | 2-pyridyl | O | 1 | OCH$_3$ | CH$_3$ | N | 185–186° |
| 159 | —CH$_2$— | —CO—C$_3$H$_7$—i | O | 1 | OCH$_3$ | CH$_3$ | CH | 122–130° |
| 160 | — | 2-pyridyl | O | 0 | OCH$_3$ | CH$_3$ | CH | |
| 161 | — | 2-pyridyl | O | 0 | OCH$_3$ | OCH$_3$ | CH | |
| 162 | — | 2-pyridyl | O | 0 | OCH$_3$ | CH$_3$ | N | |
| 163 | — | 2-pyridyl | O | 0 | OCH$_3$ | OCH$_3$ | N | |
| 164 | —(CH$_2$)$_3$— | —COOC$_2$H$_5$ | O | 1 | CH$_3$ | OCH$_3$ | N | 128–130° |
| 165 | —(CH$_2$)$_3$— | —COOC$_2$H$_5$ | O | 1 | CH$_3$ | OCH$_3$ | CH | |
| 166 | —(CH$_2$)$_3$— | —COOC$_2$H$_5$ | O | 1 | CH$_3$ | OCHF$_2$ | CH | |
| 167 | —(CH$_2$)$_3$— | —COOC$_2$H$_5$ | O | 1 | OCH$_3$ | OCH$_3$ | N | |
| 168 | —(CH$_2$)$_3$— | —COOC$_2$H$_5$ | O | 1 | OCH$_3$ | OCH$_3$ | CH | |
| 169 | —CH(C$_2$H$_5$)— | —COOC$_2$H$_5$ | O | 1 | CH$_3$ | OCH$_3$ | N | 118–120° |
| 170 | —CH(C$_2$H$_5$)— | —COOC$_2$H$_5$ | O | 1 | CH$_3$ | OCH$_3$ | CH | |
| 171 | —CH(C$_2$H$_5$)— | —COOC$_2$H$_5$ | O | 1 | OCH$_3$ | OCH$_3$ | CH | |
| 172 | —CH(C$_2$H$_5$)— | —COOC$_2$H$_5$ | O | 1 | OCH$_3$ | OCH$_3$ | N | |

TABLE 3-continued

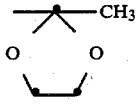

| No. | A | Q | X | m | | | E | m.p. (°C.) |
|---|---|---|---|---|---|---|---|---|
| 173 | (X)—CH₂—CH=CH—(Q) | —COOCH₃ | O | 1 | CH₃ | OCH₃ | N | 152–154° |
| 174 | (X)—CH₂—CH=CH—(Q) | —COOCH₃ | O | 1 | CH₃ | OCH₃ | CH | |
| 175 | (X)—CH₂—CH=CH—(Q) | —COOCH₃ | O | 1 | CH₃ | OCHF₂ | CH | |
| 176 | (X)—CH₂—CH=CH—(Q) | —COOCH₃ | O | 1 | CH₃ | OC₂H₅ | N | |
| 177 | (X)—CH₂—CH=CH—(Q) | —COOCH₃ | O | 1 | CH₃ | CH₃ | CH | |
| 178 | —CH₂— | oxiranyl | O | 1 | CH₃ | CH₃ | CH | |
| 179 | —CH₂— | oxiranyl | O | 1 | CH₃ | OCH₃ | N | 123° |
| 180 | —CH₂— | oxiranyl | O | 1 | CH₃ | OCH₃ | CH | 154–155° |
| 181 | —CH₂— | oxiranyl | O | 1 | CH₃ | OC₂H₅ | N | |
| 182 | —CH₂— | oxiranyl | O | 1 | CH₃ | OCHF₂ | CH | 114–116° |
| 183 | —CH₂— | oxiranyl | O | 1 | OCH₃ | OCH₃ | CH | |
| 184 | —CH₂— | oxiranyl | O | 1 | OCH₃ | OCH₃ | N | |
| 185 | —CH₂— | oxiranyl | O | 1 | CH₃ | CH₃ | CH | |
| 186 | —CH₂— | oxiranyl | S | 1 | CH₃ | OCH₃ | N | |
| 187 | —CH₂— | oxiranyl | S | 1 | CH₃ | OCH₃ | CH | |
| 188 | —CH₂— | tetrahydrofuran-2-yl | O | 1 | CH₃ | OCH₃ | CH | 141–143° |
| 189 | —CH₂— | tetrahydrofuran-2-yl | O | 1 | CH₃ | OCH₃ | N | 155–156° |
| 190 | —CH₂— | tetrahydrofuran-2-yl | O | 1 | CH₃ | OCHF₂ | CH | 158–159° |
| 191 | —CH₂— | tetrahydrofuran-2-yl | O | 1 | CH₃ | OC₂H₅ | CH | |
| 192 | —CH₂— | tetrahydrofuran-2-yl | O | 1 | OCH₃ | OCH₃ | CH | |
| 193 | —CH₂— | tetrahydrofuran-2-yl | O | 1 | OCH₃ | OCH₃ | N | |
| 194 | —CH₂— | 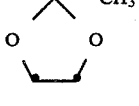 | O | 1 | OCH₃ | OCH₃ | N | |
| 195 | —CH₂— |  | O | 1 | OCH₃ | OCH₃ | CH | |
| 196 | —CH₂— | 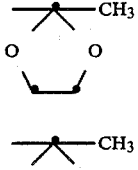 | O | 1 | CH₃ | OCH₃ | CH | |
| 197 | —CH₂— | 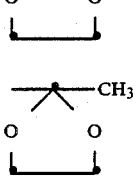 | O | 1 | CH₃ | OCH₃ | N | 158–160° |
| 198 | —CH₂— |  | O | 1 | CH₃ | OCHF₂ | CH | |
| 199 | —CH₂— | | O | 1 | OCH₃ | OCH₃ | CH | |

TABLE 3-continued

Structure:
$$\text{Ar}(X-A_m-Q)-SO_2-NH-CO-NH-C(=N-C(R_2)=)-E-(=C(R_3)-N=)$$

where the aromatic ring bears X–A$_m$–Q substituent and the sulfonylurea links to a triazine/pyrimidine ring with R$_2$, R$_3$, and E.

| No. | A | Q | X | m | R$_2$ | R$_3$ | E | m.p. (°C.) |
|---|---|---|---|---|---|---|---|---|
| 200 | —CH$_2$— | —C(CH$_3$)(O-CH$_2$-)(O-CH$_2$-) (dioxane-CH$_3$) | O | 1 | OCH$_3$ | OCH$_3$ | N | |
| 201 | —CH$_2$— | —C(CH$_3$)=N—OH | O | 1 | OCH$_3$ | CH$_3$ | N | 171–172° |
| 202 | —CH$_2$— | —C(CH$_3$)=N—OH | O | 1 | OCH$_3$ | CH$_3$ | CH | |
| 203 | —CH$_2$— | —C(CH$_3$)=N—OH | O | 1 | CH$_3$ | OCHF$_2$ | CH | |
| 204 | —CH$_2$— | —C(CH$_3$)=N—O—CH$_2$—CH=CH$_2$ | O | 1 | CH$_3$ | OCHF$_2$ | CH | |
| 205 | —CH$_2$— | —C(CH$_3$)=N—O—CH$_2$—CH=CH$_2$ | O | 1 | CH$_3$ | OCH$_3$ | CH | |
| 206 | —CH$_2$— | —C(CH$_3$)=N—O—CH$_2$—CH=CH$_2$ | O | 1 | CH$_3$ | OCH$_3$ | N | 152–154° |
| 207 | —CH$_2$— | —C(CH$_3$)=N—O—CH$_2$—CH=CH$_2$ | O | 1 | OCH$_3$ | OCH$_3$ | N | |
| 208 | —CH$_2$— | —C(CH$_3$)=N—O—CH$_2$—CH=CH$_2$ | O | 1 | OCH$_3$ | OCH$_3$ | CH | |
| 209 | —CH$_2$— | —C(CH$_3$)=N—O—CH$_2$—CH=CH$_2$ | O | 1 | CH$_3$ | CH$_3$ | CH | |
| 210 | —CH$_2$— | —C(CH$_3$)=N—OC$_2$H$_5$ | O | 1 | CH$_3$ | CH$_3$ | CH | |
| 211 | —CH$_2$— | —C(CH$_3$)=N—OC$_2$H$_5$ | O | 1 | CH$_3$ | OCH$_3$ | CH | |
| 212 | —CH$_2$— | —C(CH$_3$)=N—OC$_2$H$_5$ | O | 1 | CH$_3$ | OCH$_3$ | N | 149–152° |
| 213 | —CH$_2$— | —C(CH$_3$)=N—OC$_2$H$_5$ | O | 1 | CH$_3$ | OCHF$_2$ | CH | |
| 214 | —CH$_2$— | —C(CH$_3$)=N—OC$_2$H$_5$ | O | 1 | OCH$_3$ | OCH$_3$ | CH | |
| 215 | —CH$_2$— | —C(CH$_3$)=N—OC$_2$H$_5$ | O | 1 | OCH$_3$ | OCH$_3$ | N | |
| 216 | —CH$_2$— | —O—(CH$_2$)$_2$—OCH$_3$ | O | 1 | OCH$_3$ | OCH$_3$ | N | |
| 217 | —CH$_2$— | —O—(CH$_2$)$_2$—OCH$_3$ | O | 1 | OCH$_3$ | OCH$_3$ | CH | |
| 218 | —CH$_2$— | —O—(CH$_2$)$_2$—OCH$_3$ | O | 1 | CH$_3$ | OCH$_3$ | CH | |
| 219 | —CH$_2$— | —O—(CH$_2$)$_2$—OCH$_3$ | O | 1 | CH$_3$ | OCH$_3$ | N | 135–136° |
| 220 | —CH$_2$— | —O—(CH$_2$)$_2$—OCH$_3$ | O | 1 | CH$_3$ | OCHF$_2$ | CH | 104–106° |
| 221 | —CH$_2$— | —C(CH$_3$)=N—C$_3$H$_7$—n | O | 1 | CH$_3$ | OCH$_3$ | CH | |
| 222 | —CH$_2$— | —C(CH$_3$)=N—C$_3$H$_7$—n | O | 1 | CH$_3$ | OCH$_3$ | N | |
| 223 | —CH$_2$— | 2,2-dimethyl-1,3-dioxolan-4-yl (O-CH$_2$-C(CH$_3$)$_2$-O-CH<) | O | 1 | CH$_3$ | OCH$_3$ | N | 127–131° |
| 224 | —CH$_2$— | 2,2-dimethyl-1,3-dioxolan-4-yl | O | 1 | CH$_3$ | OCH$_3$ | CH | 141–143° |
| 225 | —CH$_2$— | 2,2-dimethyl-1,3-dioxolan-4-yl | O | 1 | CH$_3$ | OCHF$_2$ | CH | 168–169° |
| 226 | —CH$_2$— | 2,2-dimethyl-1,3-dioxolan-4-yl | O | 1 | CH$_3$ | CH$_3$ | CH | 149–150° |
| 227 | —CH$_2$— | 2,2-dimethyl-1,3-dioxolan-4-yl | O | 1 | OCH$_3$ | OCH$_3$ | CH | |

TABLE 3-continued

Structure: Ar-SO$_2$-NH-CO-NH-C(=N-C(R$_2$)=E-C(R$_3$)=N-) with X-A$_m$-Q substituent on the benzene ring.

| No. | A | Q | X | m | R$_2$ | R$_3$ | E | m.p. (°C.) |
|---|---|---|---|---|---|---|---|---|
| 228 | —CH$_2$— | dioxolane with two CH$_3$ (acetonide) | O | 1 | OCH$_3$ | OCH$_3$ | N | |
| 229 | —CH$_2$— | dioxolane-H | O | 1 | CH$_3$ | OCH$_3$ | N | |
| 230 | —CH$_2$— | dioxolane-H | O | 1 | CH$_3$ | OCH$_3$ | CH | |
| 231 | —CH$_2$— | dioxolane-H | O | 1 | CH$_3$ | OCHF$_2$ | CH | |
| 232 | —CH$_2$— | dioxolane CH$_3$/C$_2$H$_5$ | O | 1 | CH$_3$ | OCHF$_2$ | CH | 75–78° |
| 233 | —CH$_2$— | dioxolane CH$_3$/C$_2$H$_5$ | O | 1 | CH$_3$ | OCH$_3$ | CH | 150–151° |
| 234 | —CH$_2$— | dioxolane CH$_3$/C$_2$H$_5$ | O | 1 | CH$_3$ | OCH$_3$ | N | 133–134° |
| 235 | —CH$_2$— | dioxolane CH$_3$/C$_2$H$_5$ | O | 1 | CH$_3$ | CH$_3$ | CH | 95–99° |
| 236 | —CH$_2$— | oxirane-CH$_3$ | O | 1 | CH$_3$ | CH$_3$ | CH | 146–147° |
| 237 | —CH$_2$— | oxirane-CH$_3$ | O | 1 | CH$_3$ | OCH$_3$ | CH | 151–152° |
| 238 | —CH$_2$— | oxirane-CH$_3$ | O | 1 | CH$_3$ | OCH$_3$ | N | 149–151° |
| 239 | —CH$_2$— | oxirane-CH$_3$ | O | 1 | CH$_3$ | OCHF$_2$ | CH | 130–132° |

TABLE 3-continued

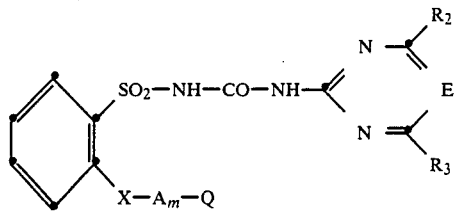

| No. | A | Q | X | m | | | E | m.p. (°C.) |
|---|---|---|---|---|---|---|---|---|
| 240 | —CH₂— | ⌬—CH₃ (epoxide) | O | 1 | CH₃ | OC₂H₅ | N | |
| 241 | —CH₂— | ⌬—CH₃ (epoxide) | O | 1 | CH₃ | OC₂H₅ | N | |
| 242 | —CH₂— | ⌬—CH₃ (epoxide) | O | 1 | CH₃ | OCH₃ | N | 127–129° |
| 243 | —CH₂— | ⌬—CH₃ (epoxide) | O | 1 | CH₃ | OCH₃ | CH | 127–128° |
| 244 | —CH₂— | ⌬—CH₃ (epoxide) | O | 1 | CH₃ | OCHF₂ | CH | 120–122° |
| 245 | —CH₂— | ⌬—CH₃ (epoxide) | O | 1 | CH₃ | CH₃ | CH | 155–156° |
| 246 | —CH₂— | —C(C₃H₇—i)=N—OC₂H₅ | O | 1 | CH₃ | OCH₃ | CH | |
| 247 | —CH₂— | —C(C₃H₇—i)=N—OC₂H₅ | O | 1 | CH₃ | OCH₃ | N | |
| 248 | —CH₃— | dioxolane-C₃H₇—i | O | 1 | CH₃ | OCH₃ | N | |
| 249 | —CH₂— | dioxolane-C₃H₇—i | O | 1 | CH₃ | OCH₃ | CH | |
| 250 | —CH₂—CH₂— | —O—CO—CH₃ | O | 1 | CH₃ | OCH₃ | CH | |
| 251 | —CH₂—CH₂— | —O—CO—CH₃ | O | 1 | OCH₃ | OCH₃ | CH | |
| 252 | —CH₂—CH₂— | —O—CO—CH₃ | O | 1 | OCH₃ | OCH₃ | N | |
| 253 | —CH₂—CH₂— | —O—CO—CH₃ | O | 1 | OCH₃ | OCHF₂ | CH | |
| 254 | —CH₂—CH₂— | —O—CO—CH₃ | O | 1 | CH₃ | CH₃ | CH | |
| 255 | —CH₂—CH₂— | —O—CO—CH₃ | S | 1 | CH₃ | OCH₃ | CH | |
| 256 | —CH₂—CH₂— | —O—CO—CH₃ | S | 1 | OCH₃ | OCH₃ | CH | |
| 257 | —CH₂—CH₂— | —O—CO—CH₃ | S | 1 | CH₃ | CH₃ | CH | |
| 258 | —CH₂—CH₂— | —O—CO—CH₃ | S | 1 | CH₃ | OCHF₂ | CH | |
| 259 | —CH₂—CH₂— | —O—CO—CH₃ | S | 1 | OCH₃ | OCH₃ | N | |
| 260 | —CH₂—CH₂— | —O—CO—CH₃ | SO₃ | 1 | CH₃ | OCH₃ | CH | |
| 261 | —CH₂—CH₂— | —O—CO—CH₃ | SO₃ | 1 | OCH₃ | OCH₃ | CH | |
| 262 | —CH₂—CH₂— | —O—CO—CH₃ | SO₃ | 1 | CH₃ | CH₃ | CH | |
| 263 | —CH₂—CH₂— | —O—CO—CH₃ | SO₃ | 1 | CH₃ | OCHF₂ | CH | |
| 264 | —CH₂—CH₂— | —O—CO—CH₃ | SO₃ | 1 | OCH₃ | OCH₃ | N | |
| 265 | —CH₂—CH₂— | OH | O | 1 | CH₃ | OCH₃ | CH | |
| 266 | —CH₂—CH₂— | OH | O | 1 | CH₃ | OCHF₂ | CH | |
| 267 | —CH₂—CH₂— | OH | O | 1 | OCH₃ | OCH₃ | N | |
| 268 | —CH₂—CH₂— | —N(CH₃)₂ | O | 1 | CH₃ | OCHF₂ | CH | |
| 269 | —CH₂—CH₂— | —N(CH₃)₂ | O | 1 | CH₃ | OCH₃ | N | |
| 270 | —CH₂—CH₂— | —O—SO₂—CH₃ | O | 1 | CH₃ | OCH₃ | CH | |
| 271 | —CH₂—CH₂— | —O—SO₂—CH₃ | O | 1 | OCH₃ | OCH₃ | CH | |
| 272 | —CH₂—CH₂— | —O—SO₂—CH₃ | O | 1 | CH₃ | OCHF₂ | CH | |
| 273 | —CH₂—CH₂— | OH | O | 1 | OC₂H₅ | OCH₃ | CH | |
| 274 | —CH₂—CH₂— | OH | O | 1 | C₂H₅ | OCH₃ | N | |
| 275 | —CH₂—CH₂— | —O—CO—C₂H₅ | O | 1 | CH₃ | OCH₃ | N | |
| 276 | —CH₂—CH₂— | —O—CO—NH—C₂H₅ | O | 1 | CH₃ | OCH₃ | N | |
| 277 | —CH₂—CH₂— | —N(C₂H₅)₂·HCl | O | 1 | OCH₃ | OCH₃ | CH | |
| 278 | —CH₂—CH₂— | —O—SO₂—C₂H₅ | O | 1 | CH₃ | OCH₃ | N | |

TABLE 3-continued

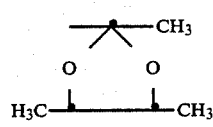

| No. | A | Q | X | m | R₁ | R₂ | E | m.p. (°C.) |
|-----|---|---|---|---|-----|-----|---|------------|
| 279 | —CH₂—CH₂— | —O—CO—C₂H₅ | S | 1 | CH₃ | OCH₃ | N | |
| 280 | —CH₂—CH₂— | —O—CO—C₂H₅ | SO₃ | 1 | CH₃ | OCH₃ | N | |
| 281 | — | —CO—N(CH₃)₂ | O | 0 | CH₃ | C₂H₅ | N | |
| 282 | —CH₂—CH₂— | —O—(CH₂)₂—OCH₃ | O | 1 | CH₃ | OCH₃ | N | 119–120° |
| 283 | — | tetrahydrofuran-3-yl | O | 0 | CH₃ | OCH₃ | N | |
| 284 | — | tetrahydrofuran-3-yl | O | 0 | CH₃ | OCH₃ | CH | |
| 285 | — | tetrahydrofuran-3-yl | S | 0 | CH₃ | OCH₃ | N | |
| 286 | — | tetrahydrofuran-3-yl | SO₂ | 0 | CH₃ | OCH₃ | N | |
| 287 | —CH₂— | thien-2-yl | O | 1 | CH₃ | OCH₃ | N | 194–195° |
| 288 | —CH₂— | thien-2-yl | O | 1 | CH₃ | OCH₃ | CH | 207–208° |
| 289 | —CH₂— | thien-2-yl | O | 1 | CH₃ | OCHF₂ | CH | 185–186° |
| 290 | —CH₂— | thien-2-yl | O | 1 | CH₃ | CH₃ | CH | 195–197° |
| 291 | —CH₂— | thien-2-yl | O | 1 | CH₃ | OC₂H₅ | N | |
| 292 | —CH₂— | thien-2-yl | O | 1 | OCH₃ | OCH₃ | N | |
| 293 | —CH₂— | thien-2-yl | O | 1 | OCH₃ | OCH₃ | CH | |
| 294 | —CH₂— | 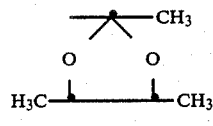 | O | 1 | CH₃ | OCH₃ | N | 151–152° |
| 295 | —CH₂— | 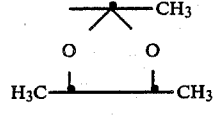 | O | 1 | CH₃ | OCH₃ | CH | 147–148° |
| 296 | —CH₂— | 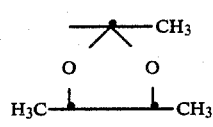 | O | 1 | CH₃ | OCHF₂ | CH | 133–136° |
| 297 | —CH₂— | 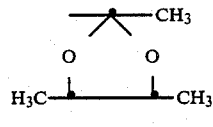 | O | 1 | CH₃ | CH₃ | CH | |
| 298 | —CH₂— | 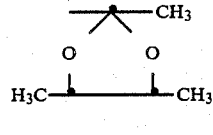 | O | 1 | CH₃ | OC₂H₅ | CH | |
| 299 | —CH₂— | 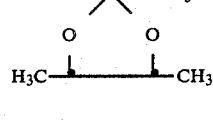 | O | 1 | OCH₃ | OCH₃ | CH | |
| 300 | —CH₂— | | O | 1 | OCH₃ | OCH₃ | N | |

TABLE 3-continued

Structure: Aryl-SO₂-NH-CO-NH-C(=N-CR₂)(=N-CR₃) triazine/pyrimidine with X-Aₘ-Q substituent on ring, E bridging atom.

| No. | A | Q | X | m | R₂ | R₃ | E | m.p. (°C.) |
|---|---|---|---|---|---|---|---|---|
| 301 | —CH₂— | dioxane-CH₃, n-C₃H₇ | O | 1 | OCH₃ | OCH₃ | N | |
| 302 | —CH₂— | dioxane-CH₃, n-C₃H₇ | O | 1 | OCH₃ | OCH₃ | CH | |
| 303 | —CH₂— | dioxane-CH₃, n-C₃H₇ | O | 1 | CH₃ | OCH₃ | CH | 142–143° |
| 304 | —CH₂— | dioxane-CH₃, n-C₃H₇ | O | 1 | CH₃ | OCH₃ | N | 126–128° |
| 305 | —CH₂— | dioxane-CH₃, n-C₃H₇ | O | 1 | CH₃ | OCHF₂ | CH | 108–112° |
| 306 | —CH₂— | dioxane-CH₃, n-C₃H₇ | O | 1 | CH₃ | CH₃ | CH | 108–110° |
| 307 | —CH₂— | dioxane-CH₃, (CH₃)₂ | O | 1 | CH₃ | CH₃ | CH | 167–168° |
| 308 | —CH₂— | dioxane-CH₃, (CH₃)₂ | O | 1 | CH₃ | OCH₃ | CH | 153–154° |
| 309 | —CH₂— | dioxane-CH₃, (CH₃)₂ | O | 1 | CH₃ | OCH₃ | N | 137–139° |

TABLE 3-continued

Structure: benzene ring with SO₂—NH—CO—NH—C(=N-R₂)(E)(=N-R₃) substituent and X—A$_m$—Q substituent

| No. | A | Q | X | m | R₂ | R₃ | E | m.p. (°C.) |
|---|---|---|---|---|---|---|---|---|
| 310 | —CH₂— | CH with two O linked to C(CH₃)₂ (dioxane-type) | O | 1 | CH₃ | OCHF₂ | CH | 138–140° |
| 311 | —CH₂— | C(CH₃) with two O linked to C(CH₃)₂ | O | 1 | OCH₃ | OCH₃ | N | |
| 312 | —CH₂— | C(CH₃) with two O linked to C(CH₃)₂ | O | 1 | OCH₃ | OCH₃ | N | |
| 313 | —CH₂— | 2-methylpyridyl | O | 1 | OCH₃ | OCH₃ | N | |
| 314 | —CH₂— | 2-methylpyridyl | O | 1 | OCH₃ | OCH₃ | CH | |
| 315 | —CH₂— | 2-methylpyridyl | O | 1 | CH₃ | OCH₃ | CH | |
| 316 | —CH₂— | 2-methylpyridyl | O | 1 | CH₃ | OCH₃ | N | |
| 317 | —CH₂— | 2-methylpyridyl | O | 1 | CH₃ | OCHF₂ | CH | |
| 318 | —CH₂— | 2-methylpyridyl | O | 1 | CH₃ | CH₃ | CH | |
| 319 | —CH₂—CH₂— | 2-pyridyl | O | 1 | CH₃ | OCH₃ | N | |
| 320 | —CH₂—CH₂— | 2-pyridyl | O | 1 | CH₃ | OCH₃ | CH | |
| 321 | —CH₂—CH₂— | 2-pyridyl | O | 1 | CH₃ | OCHF₂ | CH | |
| 322 | —CH₂—CH₂— | 2-pyridyl | O | 1 | CH₃ | CH₃ | CH | |
| 323 | —CH₂—CH₂— | 2-pyridyl | O | 1 | OCH₃ | OCH₃ | CH | |

TABLE 3-continued

Structure: benzene ring with SO$_2$—NH—CO—NH—C(=N-C(R$_2$)=E-C(R$_3$)=N-) and substituent X—A$_m$—Q on the ring

| No. | A | Q | X | m | R$_2$ | R$_3$ | E | m.p. (°C.) |
|---|---|---|---|---|---|---|---|---|
| 324 | —CH$_2$—CH$_2$— | 2-pyridyl | O | 1 | OCH$_3$ | OCH$_3$ | N | |
| 325 | —CH$_2$— | tetrahydropyran-2-yl | O | 1 | CH$_3$ | OCH$_3$ | N | 128–130° |
| 326 | —CH$_2$— | tetrahydropyran-2-yl | O | 1 | CH$_3$ | OCH$_3$ | CH | 154–155° |
| 327 | —CH$_2$— | tetrahydropyran-2-yl | O | 1 | CH$_3$ | OCHF$_2$ | CH | 122–125° |
| 328 | —CH$_2$— | tetrahydropyran-2-yl | O | 1 | CH$_3$ | CH$_3$ | CH | 155–156° |

TABLE 4

Structure: benzene ring with R$_1$ substituent, SO$_2$—NH—CO—NH—C(=N-C(R$_2$)=E-C(R$_3$)=N-) and X—A$_m$—Q

| No. | A | Q | X | m | R$_1$ | R$_2$ | R$_3$ | E | m.p. (°C.) |
|---|---|---|---|---|---|---|---|---|---|
| 401 | —CH$_2$— | —COOCH$_3$ | O | 1 | 5-CH$_3$ | OCH$_3$ | —N(CH$_3$)$_2$ | N | 192–195° |
| 402 | —CH$_2$— | —COOCH$_3$ | O | 1 | 5-CH$_3$ | OCH$_3$ | CH$_3$ | CH | 178–180° |
| 403 | —CH$_2$—CH$_2$— | —CN | O | 1 | 5-Cl | CH$_3$ | CH$_3$ | N | |
| 404 | —CH$_2$—CH$_2$— | —CN | S | 1 | 5-Cl | OCH$_3$ | OCH$_3$ | CH | |
| 405 | — | —SO$_2$—CH$_3$ | O | 0 | 5-Cl | OCH$_3$ | CH$_3$ | N | |

FORMULATION EXAMPLES

EXAMPLE 4

Formulation examples for solid active ingredients of the formula I (throughout, percentages are by weight)

| (a) Wettable powders | (a) | (b) | (c) |
|---|---|---|---|
| active ingredient | 20% | 60% | 0.5% |
| sodium lignosulfonate | 5% | 5% | 5% |
| sodium laurylsulfate | 3% | — | — |
| sodium diisobutylnaphthalene-sulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| active ingredient | 10% | 1% |
| octylphenol polyethylene glycol ether (4–5 moles of ethylene oxide) | 3% | 3% |

| (b) Emulsifiable concentrate -continued | (a) | (b) |
| --- | --- | --- |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
| --- | --- | --- |
| active ingredient | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
| --- | --- | --- |
| active ingredient | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
| --- | --- |
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
| --- | --- | --- |
| active ingredient | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
| --- | --- |
| active ingredient | 5% |
| isopropylamine | 1% |
| octylphenol polyethylene glycol ether (78 moles of ethylene oxide) | 3% |

| -continued | |
| --- | --- |
| (g) Salt solution | |
| water | 91% |

BIOLOGICAL EXAMPLES

EXAMPLE 5

Preemergence herbicidal activity

Plastic pots are filled with expanded vermiculite (density: 0.135 g/cm$^3$, water absorbing capacity: 0.565 1/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 lux and a relative humidity of 70%. During the germinating phase of 4 to 5 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the activity on the the plants is assessed according to the following rating:

1: plants have not emerged or are totally withered
2–3: very pronounced activity
4–6: medium activity
7–8: weak activity
9: no activity (as untreated controls).

Preemergence activity: Concentration of the test emulsion: 70.8 ppm.

| | Test plant | | | |
| --- | --- | --- | --- | --- |
| Compound | Nasturtium | Stellaria | Agrostis | Digitaria |
| 101 | 2 | 3 | 2 | 3 |
| 102 | 3 | 5 | 5 | 3 |
| 104 | 2 | 4 | 3 | 3 |
| 105 | 2 | 5 | 2 | 4 |
| 113 | 1 | 2 | 1 | 1 |
| 114 | 1 | 1 | 1 | 1 |
| 115 | 2 | 2 | 1 | 2 |
| 133 | 1 | 5 | 2 | 4 |
| 135 | 1 | 1 | 1 | 1 |
| 136 | 1 | 2 | 1 | 2 |
| 137 | 2 | 2 | 2 | 2 |
| 138 | 1 | 2 | 1 | 2 |
| 146 | 2 | 2 | 2 | 2 |
| 147 | 2 | 2 | 2 | 4 |
| 148 | 3 | 6 | 4 | 5 |
| 150 | 2 | 7 | 2 | 6 |
| 151 | 2 | 2 | 2 | 2 |
| 152 | 1 | 2 | 1 | 2 |
| 153 | 2 | 2 | 2 | 2 |

EXAMPLE 6

Postemergence herbicidal action (contact action)

A number of weeds and cultivated plants, both monocots and dicots, are sprayed postemergence, in the 4- to 6-leaf stage, with an aqueous dispersion of test compound at a rate of application of 0.5 kg a.i./ha, and then kept at 24°–26° and 45–60% relative humidity. The test is evaluated 15 days after treatment. In this test, the herbicidal action on plants treated with compounds of the formula I is marked in comparison with untreated controls (rating 1 to 5).

EXAMPLE 7

Growth inhibition of tropical cover crops

The test plants (*Psophocarpus palustris* and *Centrosema pubescens*) are reared until fully grown and then cut back to a height of 15 cm. The plants are sprayed 7 days later with an aqueous emulsion of the compound to be tested. The test plants are kept at 70% relative to humidity and 6000 lux artificial light for 14 hours per day, at day temperature of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants).

EXAMPLE 8

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of the formula I until thoroughly wetted. The concentration of test compound is up to 100 g a.i./ha. Evaluation is made about 5 weeks after application. Compared with untreated controls, the compounds of the formula I markedly increase the number and weight of the harvested siliques on the leading shoot.

EXAMPLE 9

Growth inhibition of cereals

Summer barley (*Hordeum vulgare*) and summer rye (Secale) are sown in sterilised soil in plastic beakers in a greenhouse and watered as required. The cereal shoots are treated about 21 days after sowing with an aqueous spray mixture of a compound of the formula I. The concentration is up to 100 g of active ingredient per hectare. Evaluation of the growth of the cereals is made 21 days after application. Compared with untreated controls, the new growth of the treated plants is markedly reduced (60-90% of controls) and in some plants the diameter of the stalks is increased.

EXAMPLE 10

Growth inhibition of grasses

A mixture of the process *Lolium perenne, Poa pratensis, Festuca ovina, Dactylis glomerata* and *Cynodon dactylon* is sown in plastic dishes filled with an earth/peat/sand mixture (6:3:1), in a greenhouse, and watered as required. The emergent grasses are cut back weekly to a height of 4 cm above the soil and, about 50 days after sowing and 1 day after the last cut, are sprayed with an aqueous spray mixture of a compound of the formula I. The concentration of test compound corresponds to a rate of application of 100 kg per hectare. The growth of the grasses is assessed after 21 days. Compared with untreated controls, the reduction in new growth effected by the compounds of formula I is in the region of 10-30%.

EXAMPLE 11

Test of selectivity in preemergence application

Seeds of dicot and monocot weeds and cultivated plants are sown in a greenhouse in pots of 11 cm diameter. Immediately afterwards the surface of the soil is treated with an aqueous dispersion or solution of the test compound. Concentrations of 0.500, 0.125 and 0.030 kg a.i./ha are employed. The pots are then kept in the greenhouse at 22°-25° C. and 50-70% relative humidity. The test is evaluated after 3 weeks and the activity is determined in accordance with the same rating as in Example 5.

| | Activity | | | | | |
|---|---|---|---|---|---|---|
| | Compound 125 | | | Compound 134 | | |
| | rate of application in kg a.i./ha | | | | | |
| Test plant | 0.500 | 0.125 | 0.030 | 0.500 | 0.125 | 0.030 |
| barley | 5 | 7 | 8 | — | — | — |
| wheat | 8 | 9 | 9 | 5 | 7 | 8 |
| *Alopecurus myos.* | 2 | 3 | 6 | 2 | 2 | 4 |
| *Echinochloa c.g.* | 2 | 5 | 9 | 2 | 3 | 4 |
| *Rottboellia ex.* | 2 | 2 | 4 | 2 | 4 | 6 |
| *Cyperus escul.* | 3 | 3 | 4 | 2 | 4 | 5 |
| Abutilon | 2 | 3 | 7 | 2 | 2 | 3 |
| *Sida spinosa* | 2 | 3 | 4 | — | — | — |
| Xanthium Sp. | 2 | 2 | 3 | 2 | 5 | 8 |
| *Amaranthus ret.* | 2 | 2 | 2 | — | — | — |
| Chenopodium Sp. | 2 | 3 | 6 | 2 | 3 | 3 |
| Ipomoea | 1 | 2 | 4 | 2 | 4 | 6 |
| Sinapis | 2 | 3 | 7 | 2 | 2 | 3 |
| *Chrysanthe. leuc.* | 2 | 2 | 3 | — | — | — |
| *Galium aparine* | 2 | 5 | 8 | 3 | 4 | 4 |
| *Viola tricolor* | 2 | 2 | 3 | 3 | 3 | 4 |

—: not tested

EXAMPLE 12

Test of selectivity in postemergence application

Following the test procedure of Example 6, a large number of plants are treated with different concentrations of test compound. Evaluation is made in accordance with the rating of Example 5.

| | Activity | | | | | |
|---|---|---|---|---|---|---|
| | Compound 125 | | | Compound 134 | | |
| | rate of application in kg a.i./ha | | | | | |
| Test plant | 0.500 | 0.125 | 0.030 | 0.500 | 0.125 | 0.030 |
| wheat | 8 | 9 | 9 | 4 | 8 | 9 |
| *Alopecurus myos.* | 2 | 3 | 5 | 3 | 5 | 8 |
| *Echinochloa c.g.* | 2 | 5 | 7 | 2 | 3 | 4 |
| *Rottboellia ex.* | 3 | 4 | 7 | 3 | 4 | 5 |
| *Cyperus escul.* | 3 | 4 | 6 | 3 | 3 | 4 |
| Abutilon | 2 | 2 | 4 | 3 | 3 | 4 |
| Xanthium Sp. | 1 | 1 | 2 | 2 | 2 | 4 |
| Chenopodium Sp. | 2 | 4 | 6 | 3 | 3 | 4 |
| Ipomoea | 2 | 3 | 3 | 5 | 7 | 7 |
| Sinapis | 2 | 2 | 2 | 3 | 3 | 3 |

We claim:

1. A compound selected from the group consisting of a sulfonylurea of the formula:

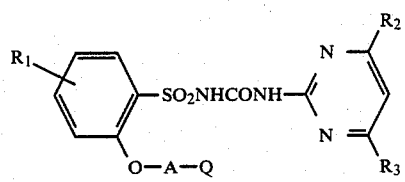

wherein
- R$_1$ is hydrogen, halo, nitro, alkyl of 1 to 4 carbon atoms, haloalkyl of 1 to 4 carbon atoms, alkoxy of 1 to 4 carbon atoms, alkenyl of 2 to 5 carbon atoms, or alkoxycarbonyl of 1 to 4 carbon atoms in the alkoxy group;
- R$_2$ is alkyl or alkoxy, each of 1 to 3 carbon atoms, unsubstituted or substituted with 1 to 3 halogen atoms;
- R$_3$ is halo, hydrogen, unsubstituted alkyl of 1 to 3 carbon atoms, alkyl of 1 to 3 carbon atoms substituted with alkoxy of 1 to 4 carbon atoms or with 1 to 3 halogen atoms, unsubstituted alkoxy of 1 to 3 carbon atoms, alkoxy of 1 to 3 carbon atoms substituted with methoxy, ethoxy, or 1 to 3 halogen atoms, or —NR$_4$R$_5$ in which R$_4$ is hydrogen or methyl and R$_5$ is hydrogen, methyl, ethyl, or methoxy; and
- Q is a heterocyclic ring selected from the group consisting of (a) a saturated ring of 3 to 6 members bound to A through a ring carbon atom and containing one or two non-adjacent oxygen atoms as the only hetero atoms, which ring is unsubstituted or substituted with one to three alkyl groups, each of 1 to 3 carbon atoms; (b) pyridyl, unsubstituted or substituted with chloro or methyl; and (c) thienyl; and
- A is alkylene of 1 to 4 carbon atoms; alkenylene of 2 to 4 carbon atoms; or a direct bond; and
- the alkali metal, alkaline earth metal, and organic amine salts thereof.

2. A compound according to claim 1, wherein R$_1$ is hydrogen.

3. A compound according to claim 1, wherein the substituents R$_2$ and R$_3$ together contain at most 4 carbon atoms.

4. A herbicidal and growth-regulating composition which comprises an effective amount of at least one compound according to claim 1, together with a suitable carrier therefor.

5. A method of controlling undesired plant growth, with method comprises applying thereto or to the locus thereof a herbicidally effective amount of a compound according to claim 1.

6. A method of suppressing plant growth, which method comprises applying thereto or to the locus thereof an effective amount of a compound according to claim 1.

7. A method according to claim 5 for selectively controlling weeds in crops of cultivated plants which method comprises applying the compound pre-emergence or post-emergence.

8. A method according to claim 6 for suppressing plant growth beyond the two-leaf stage which method comprises applying the compound pre-emergence.

9. A compound according to claim 1 and selected from the group consisting of a sulfonylurea of the formula:

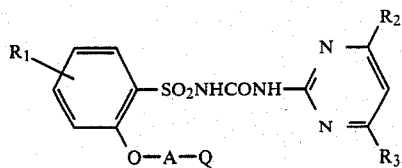

wherein
- R$_1$ is hydrogen, halo, nitro, alkyl of 1 to 4 carbon atoms, haloalkyl of 1 to 4 carbon atoms, alkoxy of 1 to 4 carbon atoms, alkenyl of 2 to 5 carbon atoms, or alkoxycarbonyl of 1 to 4 carbon atoms in the alkoxy group;
- R$_2$ is alkyl or alkoxy, each of 1 to 3 carbon atoms, unsubstituted or substituted with 1 to 3 halogen atoms;
- R$_3$ is halo, hydrogen, unsubstituted alkyl of 1 to 3 carbon atoms, alkyl of 1 to 3 carbon atoms substituted with alkoxy of 1 to 4 carbon atoms or with 1 to 3 halogen atoms, unsubstituted alkoxy of 1 to 3 carbon atoms, alkoxy of 1 to 3 carbon atoms substituted with methoxy, ethoxy, or 1 to 3 halogen atoms, or —NR$_4$R$_5$ in which R$_4$ is hydrogen or methyl and R$_5$ is hydrogen, methyl, ethyl, or methoxy;
- Q is a saturated heterocyclic ring of 3 to 6 members bound to A through a ring carbon atom and containing one or two nonadjacent oxygen atoms as the only hetero atoms, which ring is unsubstituted or substituted with one to three alkyl groups, each of 1 to 3 carbon atoms; and
- A is a direct bond, alkylene of 1 to 4 carbon atoms; alkenylene of 2 to 4 carbon atoms; or a direct bond, and
- the alkali metal, alkaline earth metal, and organic amine salts thereof.

10. A compound according to claim 9 wherein
- R$_1$ is hydrogen, methyl or chloro;
- R$_2$ is methyl or methoxy;
- R$_3$ is methyl, methoxy, chloro, difluoromethoxy, ethoxy, or dimethylamino; and
- A is alkylene of 1 to 3 carbon atoms.

11. A compound according to claim 10 wherein Q is oxiranyl; 2-methyloxiran-2-yl; 3-methyloxiran-2-yl; tetrahydrofuran-2-yl; tetrahydrofuran-3-yl; 1,3-dioxolan-2-yl; 2-methyl-1,3-dioxolan-2-yl; 2-isopropyl-1,3-dioxolan-2-yl; 2,2-dimethyl-1,3-dioxolan-4-yl; or 2-methyl-5-ethyl-1,3-dioxolan-2-yl.

12. N-(2-Oxiranylmethoxyphenylsulfonyl)-N'-(4-methoxy-6-methoylpyrimidin-2-yl)urea according to claim 11.

13. N-(2-Oxiranylmethoxyphenylsulfonyl)-N'-(4-difluoromethoxy-6-methylpyrimidin-2-yl)urea according to claim 11.

14. A compound according to claim 1 and selected from the group consisting of a sulfonylurea of the formula:

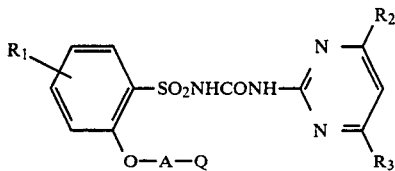

wherein
- $R_1$ is hydrogen, halo, nitro, alkyl of 1 to 4 carbon atoms, haloalkyl of 1 to 4 carbon atoms, alkoxy of 1 to 4 carbon atoms, alkenyl of 2 to 5 carbon atoms, or alkoxycarbonyl of 1 to 4 carbon atoms in the alkoxy group;
- $R_2$ is alkyl or alkoxy, each of 1 to 3 carbon atoms, unsubstituted or substituted with 1 to 3 halogen atoms;
- $R_3$ is halo, hydrogen, unsubstituted alkyl of 1 to 3 carbon atoms, alkyl of 1 to 3 carbon atoms substituted with alkoxy of 1 to 4 carbon atoms or with 1 to 3 halogen atoms, unsubstituted alkoxy of 1 to 3 carbon atoms, alkoxy of 1 to 3 carbon atoms substituted with methoxy, ethoxy, or 1 to 3 halogen atoms, or $-NR_4R_5$ in which $R_4$ is hydrogen or methyl and $R_5$ is hydrogen, methyl, ethyl, or methoxy;
- Q is pyridyl, unsubstituted or substituted with chloro or methyl, or thienyl;
- A is a direct bond, alkylene of 1 to 4 carbon atoms or alkenylene of 2 to 4 carbon atoms; and
- the alkali metal, alkaline earth metal, and organic amine salts thereof.

15. A compound according to claim 14 wherein
$R_1$ is hydrogen, methyl or chloro;
$R_2$ is methyl or methoxy;
$R_3$ is methyl, methoxy, chloro, difluoromethoxy, ethoxy, or dimethylamino; and
A is alkylene of 1 to 3 carbon atoms.

16. A compound according to claim 15 wherein Q is pyrid-2-yl, pyrid-3-yl, 3,5-dichloropyrid-2-yl, or thien-2-yl.

17. N-[2-(2,2-dimethyl-1,3-dioxolan-4-ylmethoxy)-phenylsulfonyl]-N'-(4-methoxy-6-methylpyrimidin-2-yl)urea according to claim 10.

18. N-[2-(2,2-dimethyl-1,3-dioxolan-4-ylmethoxy)-phenylsulfonyl]-N'-(4-difluoromethoxy-6-methyl-pyrimidin-2-yl)urea according to claim 10.

19. N-[2-(2-methyl-4-propyl-1,3-dioxolan-4-ylmethoxy)phenylsulfonyl]-N'-(4-difluoromethoxy-6-methylpyrimidin-2-yl)urea according to claim 10.

20. N-[2-(2,2,4-trimethyl-1,3-dioxolan-4-ylmethoxy)-phenylsulfonyl]-N'-(4-methoxy-6-methylpyrimidin-2-yl)urea according to claim 10.

21. N-[2-(2,2,4-trimethyl-1,3-dioxolan-4-ylmethoxy)-phenylsulfonyl]-N'-(4-difluoromethoxy-6-methyl-pyrimidin-2-yl)urea according to claim 10.

22. N-(2-pyridylmethoxyphenylsulfonyl)-N'-(4-methoxy-6-methylpyrimidin-2-yl)urea according to claim 16.

23. N-(3-pyridylmethoxyphenylsulfonyl)-N'-(4-methoxy-6-methylpyrimidin-2-yl)urea according to claim 16.

24. N-(2-thienylmethoxyphenylsulfonyl)-N'-(4-methoxy-6-methylpyrimidin-2-yl)urea according to claim 16.

25. N-(2-thienylmethoxyphenylsulfonyl)-N'-(4-difluoromethoxy-6-methylpyrimidin-2-yl)urea according to claim 16.

26. N-(2-thienylmethoxyphenylsulfonyl)-N'-(4,6-dimethoxypyrimidin-2-yl)urea according to claim 16.

* * * * *